United States Patent [19]
Boyd et al.

[11] Patent Number: 5,738,652
[45] Date of Patent: Apr. 14, 1998

[54] RETROGRADE DELIVERY CATHETER AND METHOD FOR INDUCING CARDIOPLEGIC ARREST

[75] Inventors: Stephen W. Boyd, Menlo Park; John H. Stevens; Philip C. Evard, both of Palo Alto; Craig L. Adams, San Ramon, all of Calif.

[73] Assignee: Heartport, Inc., Redwood City, Calif.

[21] Appl. No.: 785,079

[22] Filed: Jan. 17, 1997

Related U.S. Application Data

[60] Continuation of Ser. No. 453,595, May 30, 1995, abandoned, which is a division of Ser. No. 372,741, Jan. 12, 1995, Pat. No. 5,558,644, which is a continuation-in-part of Ser. No. 282,192, Jul. 28, 1994, Pat. No. 5,584,803, which is a continuation-in-part of Ser. No. 162,742, Dec. 3, 1993, abandoned, which is a continuation-in-part of Ser. No. 123,411, Sep. 17, 1993, abandoned, which is a continuation-in-part of Ser. No. 991,188, Dec. 15, 1992, abandoned, which is a continuation-in-part of Ser. No. 730,559, Jul. 16, 1991, Pat. No. 5,370,685.

[51] Int. Cl.$^6$ ..................................... A61M 29/00
[52] U.S. Cl. .............................. 604/96; 604/28; 604/49; 606/194
[58] Field of Search .................... 604/96, 49, 27, 604/28, 4; 606/192–194; 600/18

[56] References Cited

U.S. PATENT DOCUMENTS

| 150,960 | 5/1874 | Isbell . |
|---|---|---|
| 231,601 | 8/1880 | Meigs . |

(List continued on next page.)

FOREIGN PATENT DOCUMENTS

| WO 83/03204 | 9/1983 | European Pat. Off. . |
|---|---|---|
| 0 249 338 | 5/1987 | European Pat. Off. . |

(List continued on next page.)

OTHER PUBLICATIONS

Menasche et al. "Retrograde Coronary Sinus Cardioplegia for Aortic Valve Operations: A Clinical Report on 500 Patients" Ann Thorac Surg, 49:556–64 (1990).

Farcot et al. "New Catheter–Pump System for diastolic Synchronized Coronary Sinus Retroperfusion (D.S.R.)" Med Prog Technol, 8(1):29–37 (1980).

(List continued on next page.)

*Primary Examiner*—John D. Yasko
*Attorney, Agent, or Firm*—Jeffry J. Grainger; Jens E. Hoekendijk; Michael J. Lynch

[57] ABSTRACT

A retrograde delivery catheter includes at its distal end a balloon configured to occlude the coronary sinus of a patient's heart, and has a length and flexibility which allow the distal end to be positioned in the coronary sinus with the proximal end extending transluminally to a peripheral vein such as an internal jugular vein and out of the body through a puncture therein. The delivery catheter has a delivery lumen extending between its proximal and distal ends which is configured to allow a cardioplegic fluid to be delivered at a flow rate of at least 200 ml/min with a pump pressure less than 300 mm Hg, thereby allowing cardioplegic arrest to be maintained using a blood cardioplegic fluid without causing excessive hemolysis. In a method of inducing cardioplegic arrest according to the invention, the patient is placed on cardiopulmonary bypass, the coronary arteries are isolated from remainder of the arterial system, and the delivery catheter is positioned transluminally in the coronary sinus from a peripheral vein. A cardioplegic fluid is then delivered to the coronary sinus through the delivery catheter at a flow rate of at least 200 ml/min and a pump pressure less than 300 mm Hg. The heart may be vented by withdrawing blood from the pulmonary artery through a catheter introduced through a peripheral vein, or withdrawing blood from the aortic root through an aortic catheter introduced through a peripheral artery.

28 Claims, 7 Drawing Sheets

U.S. PATENT DOCUMENTS

| | | |
|---|---|---|
| 280,225 | 6/1883 | Noe . |
| 299,622 | 6/1884 | Chase . |
| 303,757 | 8/1884 | Sears et al. . |
| 1,282,881 | 10/1918 | Landis . |
| 2,029,236 | 1/1936 | Klophaus . |
| 2,308,484 | 1/1943 | Auzin et al. . |
| 2,531,730 | 11/1950 | Henderson . |
| 2,854,982 | 10/1958 | Pagano . |
| 3,326,648 | 6/1967 | Provisor . |
| 3,385,300 | 5/1968 | Holter . |
| 3,635,223 | 1/1972 | Klieman . |
| 3,671,979 | 6/1972 | Moulopoulos . |
| 3,674,014 | 7/1972 | Tillander . |
| 3,692,018 | 9/1972 | Goetz et al. . |
| 3,766,924 | 10/1973 | Pidgeon . |
| 3,788,328 | 1/1974 | Alley et al. . |
| 3,833,003 | 9/1974 | Taricco . |
| 3,837,347 | 9/1974 | Tower . |
| 3,889,686 | 6/1975 | Duturbure . |
| 3,903,895 | 9/1975 | Alley et al. . |
| 3,915,171 | 10/1975 | Shermeta . |
| 3,963,028 | 6/1976 | Cooley et al. . |
| 3,970,090 | 7/1976 | Loiacono . |
| 3,983,879 | 10/1976 | Todd . |
| 4,019,515 | 4/1977 | Kornblum et al. . |
| 4,029,104 | 6/1977 | Kerber . |
| 4,056,854 | 11/1977 | Boretos et al. . |
| 4,154,227 | 5/1979 | Krause et al. . |
| 4,204,328 | 5/1980 | Kutner . |
| 4,284,073 | 8/1981 | Krause et al. . |
| 4,285,341 | 8/1981 | Pollack . |
| 4,287,892 | 9/1981 | Schiff . |
| 4,290,428 | 9/1981 | Durand et al. . |
| 4,301,803 | 11/1981 | Handa et al. . |
| 4,304,239 | 12/1981 | Perlin . |
| 4,323,071 | 4/1982 | Simpson et al. . |
| 4,327,709 | 5/1982 | Hanson et al. . |
| 4,328,056 | 5/1982 | Snooks . |
| 4,351,341 | 9/1982 | Goldberg et al. . |
| 4,405,313 | 9/1983 | Sisley et al. . |
| 4,411,055 | 10/1983 | Simpson et al. . |
| 4,413,989 | 11/1983 | Schjeldahl et al. . |
| 4,417,576 | 11/1983 | Baran . |
| 4,439,186 | 3/1984 | Kuhl . |
| 4,441,495 | 4/1984 | Hicswa . |
| 4,456,000 | 6/1984 | Schjeldahl et al. . |
| 4,459,977 | 7/1984 | Pizon et al. . |
| 4,464,175 | 8/1984 | Altman et al. . |
| 4,493,697 | 1/1985 | Krause et al. . |
| 4,496,345 | 1/1985 | Hasson . |
| 4,512,762 | 4/1985 | Spears . |
| 4,531,936 | 7/1985 | Gordon . |
| 4,535,757 | 8/1985 | Webster, Jr. . |
| 4,540,399 | 9/1985 | Litzie et al. . |
| 4,552,558 | 11/1985 | Muto . |
| 4,573,966 | 3/1986 | Weikl et al. . |
| 4,601,706 | 7/1986 | Aillon . |
| 4,610,661 | 9/1986 | Possis et al. . |
| 4,648,384 | 3/1987 | Schmukler . |
| 4,689,041 | 8/1987 | Corday et al. . |
| 4,714,460 | 12/1987 | Calderon . |
| 4,721,109 | 1/1988 | Healey . |
| 4,723,936 | 2/1988 | Buchbinder et al. . |
| 4,751,924 | 6/1988 | Hammerschmidt et al. . |
| 4,753,637 | 6/1988 | Horneffer . |
| 4,770,652 | 9/1988 | Mahurkar . |
| 4,771,777 | 9/1988 | Horzewski . |
| 4,790,825 | 12/1988 | Bernstein et al. . |
| 4,796,629 | 1/1989 | Grayzel . |
| 4,804,358 | 2/1989 | Karcher et al. . |
| 4,804,365 | 2/1989 | Litzie et al. . |
| 4,808,165 | 2/1989 | Carr . |
| 4,811,737 | 3/1989 | Rydell . |
| 4,821,722 | 4/1989 | Miller et al. . |
| 4,848,344 | 7/1989 | Sos et al. . |
| 4,850,969 | 7/1989 | Jackson . |
| 4,877,031 | 10/1989 | Conway et al. . |
| 4,877,035 | 10/1989 | Bogen et al. . |
| 4,889,137 | 12/1989 | Kolobow . |
| 4,898,168 | 2/1990 | Yule . |
| 4,917,667 | 4/1990 | Jackson . |
| 4,923,450 | 5/1990 | Maeda et al. . |
| 4,927,412 | 5/1990 | Menasche . |
| 4,934,996 | 6/1990 | Mohl et al. . |
| 4,943,277 | 7/1990 | Bolling . |
| 4,990,143 | 2/1991 | Sheridan . |
| 4,994,032 | 2/1991 | Sugiyama et al. . |
| 4,994,033 | 2/1991 | Shockey et al. . |
| 5,009,636 | 4/1991 | Wortley et al. . |
| 5,011,469 | 4/1991 | Buckberg et al. . |
| 5,013,296 | 5/1991 | Buckberg et al. . |
| 5,021,044 | 6/1991 | Sharkawy . |
| 5,021,045 | 6/1991 | Buckberg et al. . |
| 5,024,668 | 6/1991 | Peters et al. . |
| 5,033,998 | 7/1991 | Corday et al. . |
| 5,041,093 | 8/1991 | Chu . |
| 5,041,098 | 8/1991 | Loiterman et al. . |
| 5,049,132 | 9/1991 | Shaffer et al. . |
| 5,059,167 | 10/1991 | Lundquist et al. . |
| 5,106,368 | 4/1992 | Uldall et al. . |
| 5,112,305 | 5/1992 | Barath et al. . |
| 5,171,232 | 12/1992 | Castillo et al. . |
| 5,197,952 | 3/1993 | Marcadis et al. . |
| 5,219,326 | 6/1993 | Hattler . |
| 5,226,427 | 7/1993 | Buckberg et al. . |
| 5,236,413 | 8/1993 | Feiring . |
| 5,250,069 | 10/1993 | Nobuyoshi et al. . |
| 5,254,089 | 10/1993 | Wang . |
| 5,308,320 | 5/1994 | Safar et al. . |
| 5,324,260 | 6/1994 | O'Neill et al. . |
| 5,370,640 | 12/1994 | Kolff . |
| 5,374,245 | 12/1994 | Mahurkar . |
| 5,380,282 | 1/1995 | Burns . |
| 5,385,548 | 1/1995 | Williams et al. . |
| 5,395,330 | 3/1995 | Marcadis et al. . |
| 5,411,027 | 5/1995 | Wiklund et al. . |
| 5,423,772 | 6/1995 | Lurie et al. . |
| 5,451,207 | 9/1995 | Yock . |
| 5,487,730 | 1/1996 | Marcadis et al. . |
| 5,488,960 | 2/1996 | Toner . |
| 5,505,698 | 4/1996 | Booth et al. . |
| 5,525,388 | 6/1996 | Wand et al. . |
| 5,527,292 | 6/1996 | Adams et al. . |
| 5,549,581 | 8/1996 | Lurie et al. . |
| 5,558,644 | 9/1996 | Boyd et al. ........................ 604/96 |
| 5,597,377 | 1/1997 | Aldea . |

FOREIGN PATENT DOCUMENTS

| | | |
|---|---|---|
| WO 89/10155 | 11/1989 | European Pat. Off. . |
| WO 93/07927 | 10/1992 | European Pat. Off. . |
| WO 95/30447 | 11/1995 | European Pat. Off. . |
| 334404 | 1/1936 | Italy . |
| 0 335 205 | 1/1985 | Italy . |
| 1097881 | 3/1965 | United Kingdom . |
| 1097882 | 3/1965 | United Kingdom . |
| 1284701 | 4/1971 | United Kingdom . |
| 1 414 344 | 5/1973 | United Kingdom . |
| 1 467 976 | 3/1974 | United Kingdom . |
| 1 477 665 | 4/1974 | United Kingdom . |
| 1 513 918 | 8/1975 | United Kingdom . |
| WO 81/03613 | 12/1981 | WIPO . |
| WO 95/30447 | 11/1995 | WIPO . |

OTHER PUBLICATIONS

Markov et al. "Reversal of acute myocardial ischemia in closed chest animals by retrograde perfusion of the coronary sinus with arterial blood," Acta Cardiologica, XXXI(3):185–199 (1976).

Meerbaum et al. "Diastolic Retroperfusion of Acutely Ischemic Myocardium", Am J Cardiol 37:588–598 (1976).

Gundry, S.R. "Modifications of myocardial ischemia in normal and hypertrophied hearts utilizing diastolic retroperfusion of the coronary veins," J Thorac Cardiovasc Surg, 83:659–669 (1982).

Shumway, N.E. "Forward versus retrograde coronary perfusion for direct vision surgery of acquired aortic valvular disease" J Thoracic and Cardiovasc Surg, 75–80 (1959).

Kalmbach et al. "Cardioplegia delivery by combined aortic root and coronary sinus perfusion" Ann Thorac Surg, 47:316–317 (1989).

Menasche et al. "Cardioplegia by way of the coronary sinus for valvular and coronary surgery" JACC 18(2):628–636 (1991).

Drinkwater et al. "The use of combined antegrade–retrograde infusion of blood cardioplegic solution in pediatric patients undergoing heart operations" Thorac and Cardiovascular Surg, 104(5):1349–1355 (1992).

Hammond et al. "Retrograde coronary sinus perfusion: A method of myocardial protection in the dog during left coronary artery occlusion" Ann Surg 166(1):139–147 (1967).

Douville et al. "Retrograde versus antegrade cardioplegia: Impact on right ventricular function" Ann Thorac Surg 54:56–61 (1992).

Menasche et al. "Retrograde cardioplegia through the coronary sinus" Ann Thorac Surg, 44:214–216 (1987).

Menasche et al. "Retrograde warm blood cardioplegia preserves hypertrophied myocardium: A clinical study" Ann Thorac Surg 57:1429–1435 (1994).

Worldwide Medical Innovations, Instrument Listings, pp. 5–9.

Elecath, "Bain Coronary Sinus Flow Catheter for Jugular Entry," Catalog No. 75–2337, 1994.

Research Medical, Inc. Product Catalog 1995, Cardioplegia Products.

Farcot et al., "Synchronized Retroperfusion of Coronary Veins for Circulatory Support of Jeopardized Ischemic Myocardium," The American Journal of Cardiology, 1978;41:1191–1201.

Haendchen et al., "Prevention of Ischemic Injury and Early Reperfusion Derangements by Hypothermic Retroperfusion," J Am Coll Cardiol, 1983;1(4):1067–1080.

Meerbaum et al., "Hypothermic Coronary Venous Phased Retroperfusion: A Closed–chest Treatment of Acute Regional Myocardial Ischemia," Circulation, 1982;65(7):1435–1445.

Meerbaum et al., Retrograde Lysis of Coronary Artery Thrombus by Coronary Venous Strptokinase Administration, J Am Coll Cardiol, 1983;1(5):1262–1267.

Kar and Nordlander, "Coronary Veins: An Alternate Route to Ischemic Myocardium," Heart and Lung, Mar. 1992, vol. 21, No. 2, pp. 148–155.

Ropchan et al., "Salvage of Ischemic Myocardium by Non-synchronized Retroperfusion in the Pig," The Journal of Thoracic and Cardiovascular Surgery, Sep. 1992, vol. 104, No. 3, pp. 619–625.

Rossi et al. "Long–term cardiopulmonary bypass by peripheral cannulation in a model of total heart failure", J. Thorac Cardiovasc Surg, 100:914–921 (1900).

Corday et al. "Symposium on the Present Status of Reperfusion of the Acutely Ischemic Myocardium. Part I" J Am Coll Cardiol 1(4):1031–6 (1983).

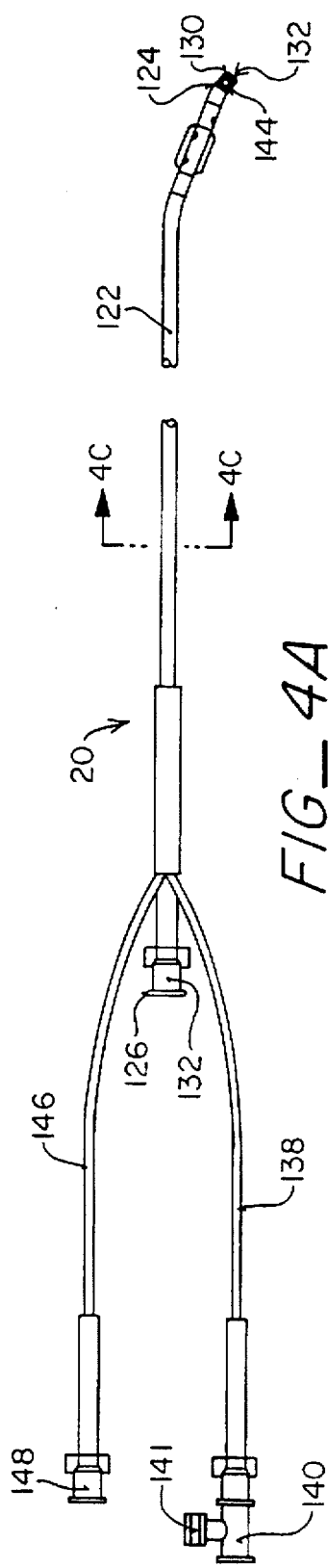
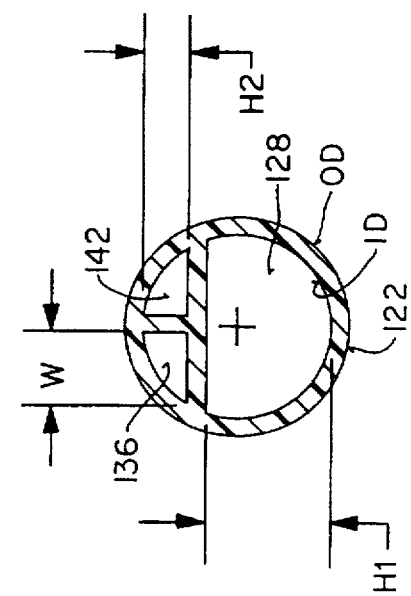
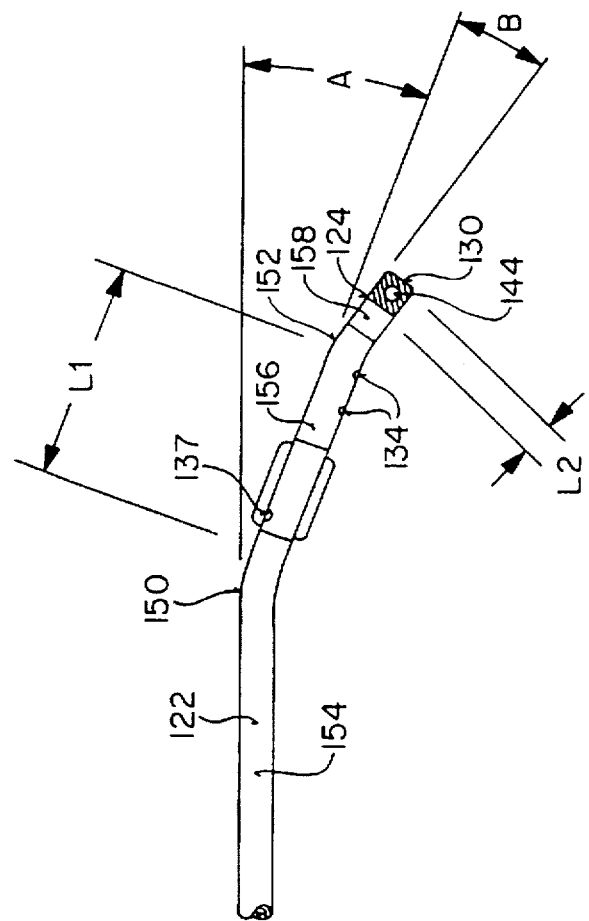
FIG_4A
FIG_4C
FIG_4B

RETROGRADE DELIVERY CATHETER AND METHOD FOR INDUCING CARDIOPLEGIC ARREST

CROSS-REFERENCE TO RELATED APPLICATIONS

This is a Continuation of application Ser. No. 08/453,595, filed May 30, 1995, now abandoned which is a division of Ser. No. 08/372,741 filed Jan. 12, 1995 now U.S. Pat. No. 5,558,644 which is a continuation-in-part of application Ser. No. 08/282,192, filed Jul. 28, 1994 now U.S. Pat. No. 5,584,803 which is a continuation-in-part of Ser. No. 08/162,742, filed Dec. 3, 1993, now abandoned which is a continuation-in-part of Ser. No. 08/123,411, filed Sep. 17, 1993, now abandoned which is a continuation-in-part of Ser. No. 07/991,188, filed Dec. 15, 1992, now abandoned which is a continuation-in-part of Ser. No. 07/730,559, filed Jul. 16, 1991 now U.S. Pat. No. 5,370,685. The complete disclosures of all of these related applications are incorporated herein by reference for all purposes.

FIELD OF THE INVENTION

This invention relates generally to devices and techniques for performing cardiac procedures and particularly to catheter systems and methods for inducing cardioplegic arrest to facilitate the performance of cardiac procedures.

BACKGROUND OF THE INVENTION

Of the various forms of heart disease, coronary artery disease and heart valve disease are two of the most widespread and debilitating. In coronary artery disease, growth of stenotic plaque in the coronary arteries causes the arterial lumen to narrow or close, restricting or cutting off blood flow to the heart muscle. Heart valve disease includes two major categories, namely stenosis, which is an obstruction to forward blood flow caused by a heart valve, and regurgitation, which is the retrograde leakage of blood through a heart valve.

The major surgical intervention for treatment of coronary artery disease is coronary artery bypass grafting, or CABG. In this procedure, while the patient is under general anesthesia, a median sternotomy or other gross thoracotomy is made, the patient is placed on cardiopulmonary bypass, and the heart is placed under cardioplegic arrest.

An arterial or vein graft is then attached between a source of arterial blood, such as the aorta, and the diseased coronary artery downstream of the stenotic region, thereby providing a blood bypass around the stenotic region. While CABG generally has high efficacy, it is highly traumatic and has a significant complication rate associated with thoracotomy.

Similarly, when it is necessary to repair or replace a malfunctioning heart valve within a patient, heretofore the repair or replacement has been accomplished by a major open-heart surgical procedure, requiring a gross thoracotomy, general anesthesia and full cardiopulmonary by-pass with complete cessation of cardiopulmonary activity. Such surgery usually includes about three weeks of hospitalization and months of recuperation time for the patient. The average mortality rate with this type of procedure is about five to six percent, and the complication rate is substantially higher. Descriptions of open-heart procedures for replacing heart valves can be found in *Gibbon's Surgery of the Chest*, 5th Ed., David C. Sabiston, Jr., M.D., Frank D. Spencer, M.D., 1990, Vol. II, Ch. 52, pp. 1566–1596, and *Textbook of Interventional Cardiology*, Eric J. Topol, 1990, Chs. 43–44, pp 831–867.

Various non-surgical interventions have recently been developed to treat coronary artery disease. Non-surgical interventions include angioplasty, wherein a balloon catheter is advanced into the diseased coronary artery, and a balloon at the distal end of the catheter is inflated within the narrowed portion of the arterial lumen to crush the plaque and widen the arterial lumen. Another non-surgical intervention is atherectomy, wherein a catheter having a cutting blade at its distal end is advanced into the diseased portion of the coronary artery and the plaque is cut from the arterial wall and removed in the catheter. These interventions have enjoyed only limited success due to the high rate of recurrence of stenosis in the coronary artery following the procedure.

Some progress has also been made in developing endovascular procedures involving the heart valves. For example, for patients with severe stenotic valve disease, who are too compromised to tolerate open-heart surgery to replace the heart valve as described above, surgeons have attempted endovascular balloon aortic or mitral valvuloplasty. These procedures involve endovascularly advancing a balloon dilatation catheter into the patient's vasculature until the balloon of the catheter is positioned between the valve leaflets and then inflating the balloon to split the commissures in a diseased valve with commissural fusion and to crack calcific plaques in a calcified stenotic valve. However, this method may provide only partial and temporary relief for a patient with a stenotic valve. Rapid restenosis has been found to occur following the procedure in many cases.

An endovascular treatment regimen for regurgitant heart valves, which involves valve supplantation, has been disclosed in the patent literature, but apparently the procedure has not been clinically practiced. In this procedure, it is conceived that an elongated catheter is used to insert a mechanical valve into the lumen of the aorta via entry through a distal artery, for example, the brachial or femoral artery. One such mechanical valve is described in U.S. Pat. No. 4,056,854 (Boretos et al.) that is designed to be positioned against the artery wall during forward flow, as compared to the mid-center position of the valve described in U.S. Pat. No. 3,671,979 (Moulopoulos). The valve positioned against the arterial wall is intended to reduce the stagnation of blood flow and consequent thrombus and emboli formation compared to a valve at mid-center position. The mechanical valves previously described require an elongated mounting catheter extending out of the arterial entry point to maintain the position of the valve in the descending aorta. These valves would be expected to present several problems. The valves do not provide a permanent or internalized system. Furthermore, since both involve a mechanical valve, which predisposes the patient to thrombus formation and emboli, long term anticoagulant therapy is required. A serious complication of long term anticoagulant therapy is intracranial hemorrhage. Finally, the supplemental valve is placed downstream from both the normal valve position and the coronary ostia, so normal heart and coronary artery hemodynamics are not restored.

The descriptive terms upstream and downstream, when used herein in relation to the patient's vasculature, refer to directions closer to and further from the heart in the arterial system, and the opposite in the venous system. The terms proximal and distal, when used herein in relation to instruments used in the procedure, refer to directions closer to and farther away from the operator performing the procedure.

What have been needed and heretofore unavailable are methods and systems for satisfactorily performing various cardiac surgical procedures, particularly those suitable for coronary artery bypass grafting and for heart valve placement or removal and replacement, which do not require a thoracotomy. The present invention satisfies these and other needs.

SUMMARY OF THE INVENTION

The present invention is directed to a method and system for an endovascular approach for preparing a patient's heart for cardiac procedures which does not require a grossly invasive thoracotomy.

The endovascular system of the invention includes an elongated catheter having proximal and distal ends and an occluding member on a distal portion of the catheter adapted to occlude a patient's ascending aorta. The catheter preferably has an inner lumen extending within the catheter to a port in the distal end of the catheter. The catheter is adapted to be inserted into the patient's arterial system (e.g. through the femoral or brachial arteries) and to be advanced to the ascending aorta where the occluding member is expanded to occlude the aorta at that location. In so doing the left ventricle of the heart and an upstream portion of the ascending aorta are separated from the rest of the patient's arterial system. This catheter thus constitutes an endovascularly inserted, internal vascular clamp, similar in function to the external "cross-clamp" used in open-surgical procedures. The internal clamp is less traumatic to the clamped vessel, and provides a lumen or working channel through which instruments or fluids may be passed into or withdrawn from the area upstream of the end of the distal end of the clamp. The occluding member on the elongated catheter should be dimensioned so that upon expansion it will be located downstream from the ostia for the coronary arteries and upstream from the brachiocephalic artery so as to avoid blocking these arteries. In one presently preferred embodiment, the inner lumen of the occluding catheter is dimensioned to allow for the passage therethrough of instruments for performing the cardiac procedure.

Also included with the system is a cardiopulmonary by-pass system which withdraws blood from the patient's venous system, e.g. the femoral or jugular vein, removes $CO_2$ from and adds oxygen to the withdrawn blood, and then returns the oxygenated blood to the patient's arterial system, e.g. the femoral or brachial artery.

The system is also provided with means to deliver a fluid containing cardioplegic material (e.g. an aqueous solution of KCl and/or magnesium procaine and the like) through the coronary arteries so as to paralyze the myocardium.

It is also preferred to depressurize the left atrium by venting the left atrium via a catheter placed in the pulmonary artery. This catheter may actually occlude the pulmonary artery to further prevent blood from flowing to the lungs. With the heart paralyzed, the expandable member of the aortic catheter expanded within the ascending aorta, and the cardiopulmonary by-pass operating, the heart is prepared for a cardiac procedure. While a particularly attractive feature of the invention is that it prepares the heart for an endovascular procedure, the invention can also be used to prepare the heart for conventional open-heart surgery via a thoracotomy. It should also be noted that, if during an endovascular cardiac procedure in accordance with the invention it becomes necessary to perform an open-heart procedure, the patient is already fully prepared for the open-heart procedure. All that is necessary is to perform a thoracotomy to expose the patient's heart for the conventional surgical procedure.

In a presently preferred embodiment of the invention directed to endovascular cardiac procedures, the occlusion catheter is adapted to deliver instruments to be used during the procedures such as the removal of an in-place aortic valve, the insertion and placement of a new valve, and the securing of the new valve at the desired location. In these procedures, the expanded expandable member on the distal end of the occlusion catheter firmly secures the distal end of the catheter within the aorta to allow for the accurate guidance of instruments to be used during the procedure.

By partitioning the arterial system with the elongated aortic catheter in this manner, a body of clear fluid can be maintained in the aortic region upstream from the expanded distal end of the aortic catheter to facilitate the imaging, e.g. angioscopic observation, of the cardiac procedure. A continual flow of clear fluid may be directed to the surgical field in order to maintain fluid clarity sufficient for imaging the site during the procedure. The pressure of the body of irrigation fluid at the surgical site can be maintained at a level equal to or higher than the fluid pressure in the patient's left atrium to prevent the intrusion of blood from the left atrium into the left ventricle, which can interfere with the imaging. The temperature of the irrigating fluid should be about 4° C. in order to reduce myocardial oxygen demand.

In order to deliver cardioplegic fluids to the myocardium, it is presently preferred to carry out retrograde perfusion of the coronary circulation. Using this technique, a physician will percutaneously introduce a retrograde delivery catheter through a major vein, e.g. the right internal jugular vein, and advance the catheter in the venous system until the distal end of the catheter extends into the coronary sinus through the discharge opening thereof in the right atrium. To accomplish this, the delivery catheter preferably has a length of at least about 50 cm, has an outer diameter of no more than about 4.6 mm for at least the distal 30 cm of the catheter, and has a durometer in the range of 50 to 72 Shore D. The delivery catheter may also include one or more bends near the distal end thereof to facilitate positioning the distal end in the coronary sinus. A soft tip is provided on the distal end of the catheter to reduce the risk of damaging the coronary sinus or other tissue. The shaft is preferably at least partially radiopaque to facilitate positioning the delivery catheter under fluoroscopic observation.

Preferably, the catheter has an inflatable balloon on the distal end thereof, such as those shown in U.S. Pat. No. 4,689,041, U.S. Pat. No. 4,943,277, and U.S. Pat. No. 5,021,045, which are incorporated herein by reference. In a preferred embodiment, the balloon is at least about 15 mm from the distal end of the catheter to facilitate placing the distal end in the coronary sinus and sealing the ostium thereof by inflating the balloon. The balloon may be inflated by an inflation fluid such as saline delivered through a separate inflation lumen in the catheter, or it may be self-inflating, wherein the balloon is inflated by the cardioplegic fluid delivered through the catheter, which after entering the balloon, may flow into the coronary sinus through outlet holes in the balloon and/or in the catheter shaft distal to the balloon. For a non-self-inflating balloon, a pressure limiting means such a pressure relief valve in communication with the inflation lumen may be provided to prevent overinflation of the balloon, which could injure the coronary sinus tissue.

When inflated, the balloon blocks the discharge opening of the coronary sinus to preclude loss of cardioplegic fluid therefrom. With the discharge opening of the coronary sinus blocked off, aqueous liquid or other fluid containing cardioplegic material is delivered through the catheter into the coronary sinus at sufficient pressure so that it passes into the myocardium via the capillary bed between the venous and arterial systems therein so as to paralyze the entire myocardium. A pressure lumen through the catheter and pressure port distal to the balloon may also be provided to facilitate measurement of pressure in the coronary sinus.

Cardioplegic fluid is delivered through the delivery catheter at a flow rate sufficient to maintain cardioplegic arrest by periodic or continual infusions. However, cardioplegic solution pressure within the coronary sinus should be less than 50 mm Hg to avoid tissue damage. The preferred cardioplegic fluid is a mixture of blood and a cardioplegic agent such as a potassium chloride (KCl) solution, preferably at a ratio or four parts blood to one part KCl solution (by volume). The cardioplegic solution is usually cooled to a temperature of between 4° C. and 10° C., resulting in a fluid with a viscosity in excess of 3.0 centipoise, and usually in the range of 6 to 8 centipoise. This cardioplegic fluid is infused at a preferred flow rate of at least 200 ml/min. in order to maintain cardioplegic arrest. However, the pressure at which the fluid is pumped or delivered through the delivery catheter ("pump pressure") should not exceed 300 mmHg so as to avoid excessive hemolysis of the blood component of the fluid and damage to the pump. To accomplish this, the lumen in the delivery catheter through which the cardioplegic fluid is delivered is preferably at least about 4.0 mm$^2$ in cross-sectional area from the proximal end to the distal end of the device.

After passing through the myocardium, the cardioplegic liquid will pass through the coronary arteries in a retrograde fashion to be discharged through the coronary ostia into the upstream portion of the ascending aorta, or it may drain back into the right atrium via the coronary sinus. The cardioplegic fluid which discharges from the coronary ostia will initially be very opaque due to blood being flushed out of the coronary circulation, but eventually the fluid will become clear and may be conveniently used to form and maintain the body of clear fluid at the surgical site to facilitate the imaging thereof during the procedure. In some instances, cardioplegic liquid may in addition or instead be delivered through the coronary arteries in an antegrade fashion, either via catheters placed through the coronary ostia into the coronary arteries or by delivery via the aortic catheter directly into the aortic root.

The left atrium is preferably decompressed by one or a combination of several methods. The first involves a catheter passing into the pulmonary trunk. The catheter described is advanced through the patient's venous system, e.g. through the right internal jugular vein, through the right atrium and right ventricle, and into the pulmonary trunk. This catheter can vent fluid from the pulmonary trunk via an inner lumen extending from its distal port to a port in its proximal end located outside the patient. It may be advantageous to have an inflatable member located at the distal end of the ventilation catheter. The inflatable member is dimensioned so that upon inflation it will block the pulmonary trunk while simultaneously venting the trunk through the inner lumen of the catheter, which extends through the catheter from a port in its distal end to a port in its proximal end located outside of the patient.

In an alternative method, as described in U.S. Pat. No. 4,889,137 (Kolobow) which is incorporated herein by reference, a catheter is advanced in essentially the same manner as that described above until the distal end is within the pulmonary trunk. As described in this patent, springs or other means are provided on the exterior of the catheter at the locations where the catheter will extend through the pulmonary and tricuspid valves in order to hold the valves at least partially open and thereby vent the pulmonary artery and decompress the left atrium.

In addition, any fluids in the heart not withdrawn by one of the previous methods may be withdrawn from the aortic root through a lumen in the occluding aortic catheter, or from the left ventricle through a catheter introduced through the aortic valve into the left ventricle.

The occluding aortic catheter with an expandable occluding member on the distal end, coupled with cardiopulmonary by-pass, cardioplegia delivery via the coronary sinus, and decompression of the left atrium, provides for a unique intravascular approach to a wide variety of cardiac procedures, an approach which does not require invasive thoracic or abdominal surgery. For example, the system may be used in conjunction with endovascular aortic valve replacement, thoracoscopic coronary artery bypass grafting as disclosed in copending application Ser. No. 08/023,778, filed Feb. 22, 1993, thoracoscopic mitral or aortic valve replacement as disclosed in copending application Ser. No. 08/163,241, filed Dec. 6, 1993, and other less-invasive procedures. Moreover, as mentioned, the system may even be employed in conventional open-heart procedures. These and other advantages of the invention will become more apparent from the following detailed description of the invention when taken in conjunction with the accompanying exemplary drawings.

BRIEF DESCRIPTION OF THE DRAWINGS

FIG. 4A is a side elevational view of the cardioplegia delivery catheter of FIG. 4.

FIG. 4B is a side view of a distal portion of the cardioplegia delivery catheter of FIG. 4A.

FIG. 4C is a transverse cross-section of the cardiopegia delivery catheter of FIG. 4A taken along line 4C—4C;

DETAILED DESCRIPTION OF THE INVENTION

Figure 1:
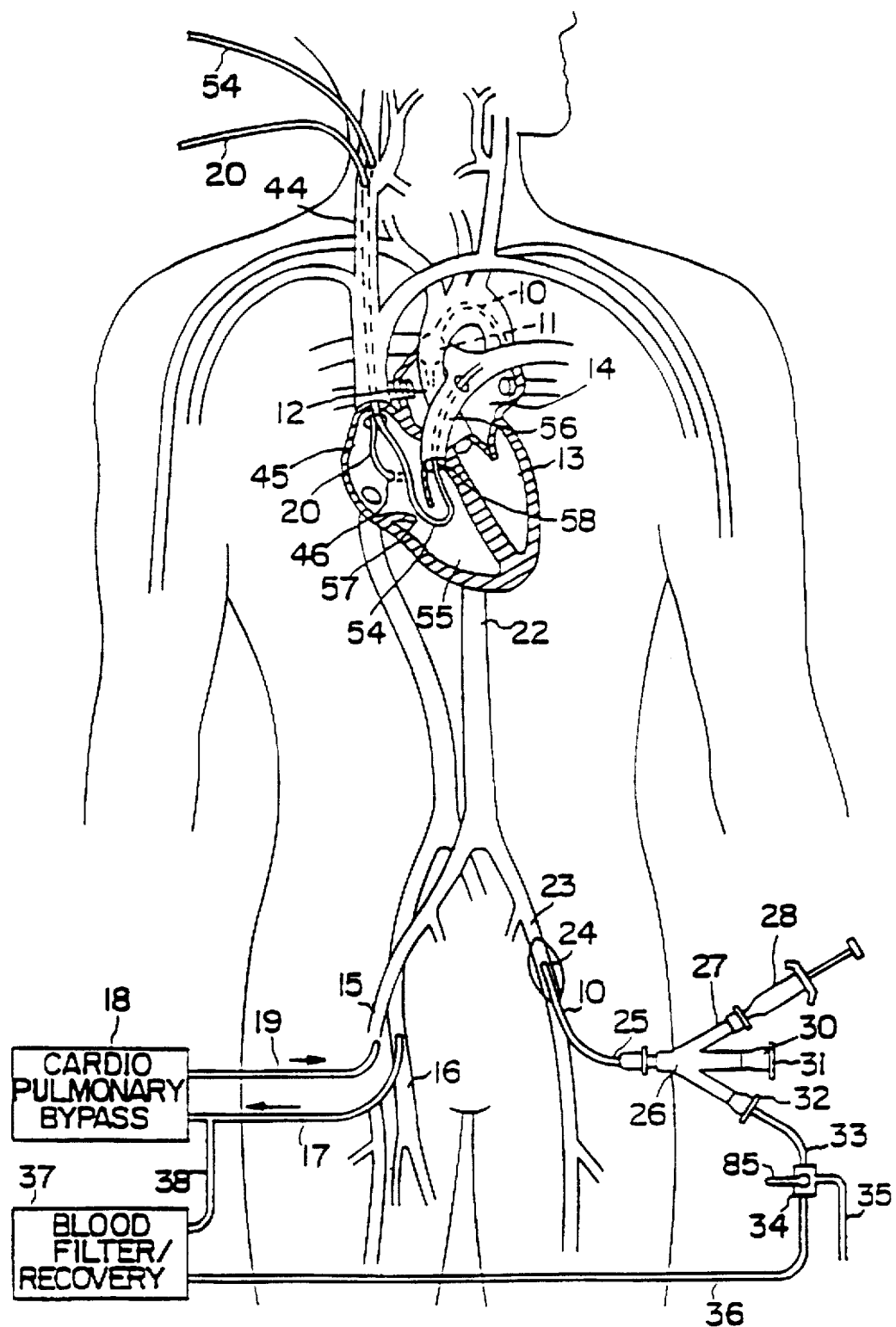
FIG. 1 schematically illustrates a cardiac access system embodying features of the invention.

Reference is made to FIG. 1 which schematically illustrates the overall cardiac accessing system of the invention and the individual components thereof. The accessing system includes an elongated aortic occlusion or delivery catheter 10 which has an expandable member 11 on a distal portion of the catheter which, when inflated as shown, occludes the ascending aorta 12 to separate the left ventricle 13 and upstream portion of the ascending aorta from the rest of the patient's arterial system and securely positions the distal end of the catheter within the ascending aorta. A cardiopulmonary by-pass system 18 removes venous blood from the femoral vein 16 through the blood withdrawal catheter 17 as shown, removes $CO_2$ from the blood, oxygenates the blood, and then returns the oxygenated blood to the patient's femoral artery 15 through the return catheter 19 at sufficient pressure so as to flow throughout the patient's arterial system except for the portion blocked by the expanded occluding member 11 on the aortic occluding catheter 10. A retrograde cardioplegia balloon catheter 20 is disposed within the patient's venous system with the distal end of the catheter extending into the coronary sinus 21 (shown in FIG. 4) to deliver a fluid containing cardioplegic agents to the myocardium in a retrograde manner through the patient's coronary venous system to paralyze the entire myocardium.

The elongated occluding catheter 10 extends through the descending aorta to the left femoral artery 23 and out of the patient through a cut down 24. The proximal extremity 25 of the catheter 10 which extends out of the patient is provided with a multi-arm adapter 26 with one arm 27 adapted to receive an inflation device 28. The adapter 26 is also provided with a second arm 30 with main access port 31 through which passes instruments, a valve prosthesis, an angioscope, irrigation fluid and the like. A third arm 32 connected to by-pass line 33 is provided to direct blood, irrigation fluid, and the like to or from the system. A suitable valve 34 is provided to open and close the by-pass line 33 and direct the fluid passing through the by-pass line to a discharge line 35 or a line 36 to a blood filter and recovery unit 37. A return line may be provided to return any filtered blood, which will be described hereinafter, to the cardiopulmonary by-pass system 18 or other blood conservation system.

Figure 3:
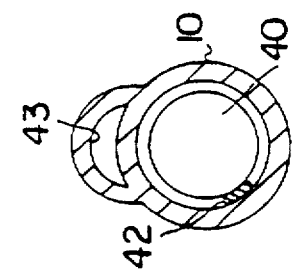
FIG. 3 is a transverse cross-sectional view of the occluding catheter shown in FIG. 2 taken along the lines 3—3.
Figure 2:
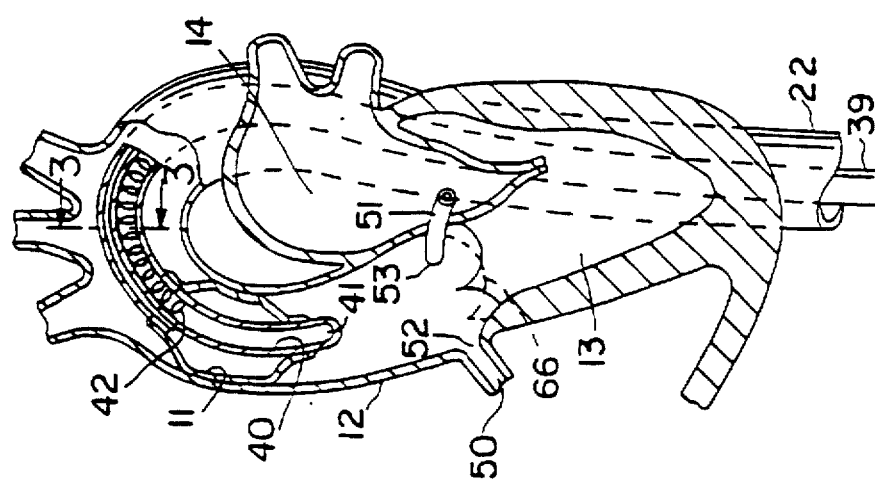
FIG. 2 is an enlarged view, partially in section, of the occluding catheter shown in FIG. 1 disposed within the ascending aorta.

The details of the aortic occlusion catheter 10 and the disposition of the distal extremity thereof within the aorta are best illustrated in FIGS. 2 and 3. As indicated, the catheter 10 includes an elongated catheter shaft 39 which has a first inner lumen 40 in fluid communication with the main access port 31 in the second arm of the adapter 26 and, in one embodiment, is adapted to facilitate the passage of instruments, a valve prosthesis, an angioscope, irrigation fluid, and the like therethrough and out the distal port 41 in the distal end thereof. A supporting coil 42 may be provided in the distal portion of the first inner lumen 40 to prevent the catheter shaft 39 from kinking as it is advanced through the aortic arch. The shaft 39 is also provided with a second inner lumen 43 which is in fluid communication with the interior of the occluding balloon 11. Preferably, shaft 39 also includes a third inner lumen (not shown in FIGS. 2–3) in communication with a pressure port distal to balloon 11 through which pressure in the aortic root may be measured, as described in co-pending application Ser. No. 08/282,192, which has been incorporated herein by reference. Shaft 39 may also have a preshaped distal end configured to conform to the shape of the aortic arch to facilitate positioning balloon 11 in the ascending aorta between the coronary ostia and the brachiocephalic artery. The preshaped distal end is straightened for introduction of the aortic occlusion catheter in a peripheral artery (e.g. a femoral artery) by a removable stylet (not shown in FIGS. 2–3) positioned in first inner lumen 40, as described in application Ser. No. 08/282,192.

A retrograde cardioplegia delivery catheter 20, which is shown in more detail in FIGS. 4 and 4A–4C, is introduced into the patient's venous system through the right internal jugular vein 44 and is advanced through the right atrium 45 and into the coronary sinus 21 through the coronary sinus discharge opening 46 in the right atrium. As shown best in FIGS. 4A–4C, retrograde delivery catheter 20 includes a flexible shaft 122 having a distal end 124, a proximal end 126 and a delivery lumen 128 extending therebetween. Shaft 122 is preferably at least about 50 cm long, and usually at least 60 cm long, between proximal end 126 and distal end 124, so that distal end 124 may be positioned in the coronary sinus with proximal end 126 extending out of the patient through a puncture in a peripheral vein such as the internal jugular vein 44. Shaft 122 is sufficiently flexible to navigate this path without difficulty, and is preferably made of a biocompatible polymer such as Pebax with a durometer in a range of 50 to 72 Shore D. Shaft 122 is preferably radiopaque to permit fluoroscopic observation thereof to facilitate positioning. Radiopaque markers may be applied to the shaft near distal end 124, or a filler such as barium sulfate may be added to the polymeric material used to form shaft 122. In order to allow percutaneous introduction of delivery catheter 20 in a peripheral vein, shaft 122 will preferably have an outer diameter OD of no more than 4.6 mm from distal end 124 to at least 30 cm proximal thereto, and usually to at least 50 cm proximal thereto. It is preferred that retrograde delivery catheter 20 be suitable for introduction through a commercially-available 9 French or 10 French introducer sheath, or for introduction by surgical cut-down into a comparably sized peripheral vein. A soft tip 130 of, for example, Pebax with a durometer of 20 to 30 Shore D is bonded to the distal end of shaft 122 to reduce the risk of trauma to the coronary sinus or other tissue.

Delivery lumen 128 extends from a fitting 132 at proximal end 126 through shaft 122 and through soft tip 130 to an outlet port 132 in the distal end of soft tip 130. Side holes 134 in communication with delivery lumen 128 may also be provided near distal end 124 of shaft 122 as shown in FIG. 4B. Delivery lumen 128 preferably has a cross-sectional area no less than about 4 mm$^2$ at any point between proximal end 126 and outlet port 132 to facilitate delivery of cardioplegic fluid at sufficient flow rates to maintain cardioplegic arrest while keeping the pressure at which the fluid is delivered low enough to avoid excessive hemolysis in the blood component of the fluid, as described more fully below. In an exemplary embodiment, the inner diameter ID of delivery lumen 128 is at least about 2.8 mm, and height H1 is at least about 1.8 mm.

The retrograde catheter 20 is provided with a balloon 47 on a distal portion of the catheter 20 which is adapted to occlude the coronary sinus 21 when inflated. Suitable balloons are described in U.S. Pat. Nos. 4,917,667, 4,927,412, and 5,021,045, which are incorporated herein by reference. In a preferred embodiment, balloon 47 is polyurethane with a maximum inflated diameter of 15 mm, an uninflated diameter of about 4.3 mm and a working length of about 6.4 mm. Balloon 47 is preferably located at least about 15 mm from distal end 124 of shaft 122 so that, during positioning, if balloon 47 is pulled out of the coronary sinus, there is sufficient length of shaft 122 distal to the balloon that will remain in the coronary sinus to eliminate the need to re-locate the coronary sinus. Balloon 47 is preferably formed by dipping a mandrel in liquefied polyurethane and curing. The balloon may be attached to shaft 122 by, for example, heat welding.

An inflation lumen 136 extends through shaft 122 and is in communication with the interior of balloon 47 through an opening 137. Near proximal end 126, inflation lumen 136 is connected to an inflation extension tube 138 attached to shaft 122 having a fitting 140 at its proximal end for attachment to an inflation fluid delivery device. Inflation lumen 136 is configured to allow delivery of inflation fluid at a sufficient rate to fully inflate balloon 47 in about 2 seconds, and preferably has a height H2 of 0.5–0.9 mm and a width w of 0.9–1.3 mm. Inflation lumen 136 may alternatively be a coaxial lumen around shaft 122, enclosed by a separate tubular member (not shown).

A pressure relief valve 141 may be connected to inflation extension tube 138 to prevent overinflation of balloon 47, which might damage the tissue of the coronary sinus. The pressure relief valve is configured to open and relieve fluid pressure from inflation lumen 136 when balloon 47 exceeds the maximum desired inflated diameter, e.g. 15 mm. This may be accomplished by pre-inflating the balloon to the maximum inflated diameter without pressure relief valve 141 mounted to the delivery catheter, thereby plastically deforming the balloon to its fully inflated size. The balloon is then collapsed onto the shaft by applying a vacuum to inflation lumen 136, and pressure relief valve 141 is mounted to inflation extension tube 138. In use, when delivery catheter is positioned in the coronary sinus, inflation of balloon 47 to the desired inflated size will require relatively low pressure, e.g. less than about 0.5–2.0 p.s.i. However, once the maximum inflated size is reached, the pressure will increase significantly, causing pressure relief valve 141 to open, thus preventing overinflation of the balloon. A suitable pressure relief valve is available from, for example, Smart Products, Inc. of San Jose, Calif., under the name "Luer Check Valve."

In an alternative embodiment, balloon 47 may be self-inflating, wherein the cardioplegic fluid itself acts as the inflation fluid for balloon 47, eliminating the need for a separate inflation lumen in shaft 122. In this embodiment, delivery lumen 128 communicates with the interior of balloon 47 in such a way that balloon 47 will inflate fully to occlude the coronary sinus only during delivery of cardioplegic fluid. For example, a fluid path between delivery lumen 128 and balloon 47 may be provided such that all or a major portion of the cardioplegic fluid delivered through delivery lumen 128 first enters the balloon to cause it to inflate, before it flows into the coronary sinus through outlet holes in shaft 122 distal to balloon 47, or through outlet holes in the balloon itself. Suitable self-inflating balloon configurations are described in U.S. Pat. Nos. 4,917,667 and 5,021,045, which have been incorporated herein by reference.

Other types of expandable members may be used instead of balloon 47. For example, a mechanically expanding mechanism may be used, such as a series of flexible beams mounted longitudinally to shaft 122 which may be deflected outward by exerting a compressive force on the beams by means of a pull wire or push rod extending through the shaft. A fluid-impervious membrane may be mounted to the beams to provide occlusion of the coronary sinus when the mechanism is expanded.

A pressure lumen 142 may also be provided in shaft 122 which opens at a pressure port 144 on a side wall of shaft 122 near distal end 124, or in soft tip 130 as illustrated. Pressure lumen 142 is connected to an extension tube 146 attached to shaft 122 near proximal end 126 and having a fitting 148 at its proximal end suitable for connection to pressure monitoring equipment. In this way, pressure in the coronary sinus distal to balloon 47 may be monitored during cardioplegic fluid delivery to ensure that pressure within the coronary sinus is maintained at a safe level. A pressure relief valve like relief valve 141 connected to inflation extension tube 138 may also be connected to delivery lumen 128 to ensure that cardioplegic fluid pressure does not exceed a predetermined level, avoiding hemolysis in the blood component of the fluid and/or protecting the coronary sinus from excessive infusion pressure.

As shown in FIG. 4B, a distal portion of shaft 122 includes a first bend 150 and a second bend 152, which facilitate the placement of distal end 124 in the coronary sinus. Second bend 152 is preferably a distance L2 of 3 mm–10 mm from the distal end of soft tip 130, and first bend 150 is a distance L1 of 20 mm–40 mm proximal to second bend 152. First and second bends 150, 152 may subtend various angles depending upon patient anatomy and surgeon preference. In a presently preferred configuration, first bend 150 subtends and angle A of between 20° and 70° relative to the longitudinal axis of a proximal portion 154 of shaft 122. Second bend 152 preferably subtends an angle B of 30° to 40° relative to a mid-portion 156 of shaft 122.

A liquid containing a cardioplegic agent, e.g. an aqueous KCl solution, is introduced into the proximal end 48 of the catheter 20, which extends outside of the patient, under sufficient pressure so that the fluid containing the cardioplegic agent can be forced to pass through the coronary sinus 21, through the capillary beds (not shown) in the patient's myocardium, through the coronary arteries 50 and 51 and ostia 52 and 53 associated with the respective coronary arteries into the blocked off portion of the ascending aorta 12 as shown.

Figure 4:
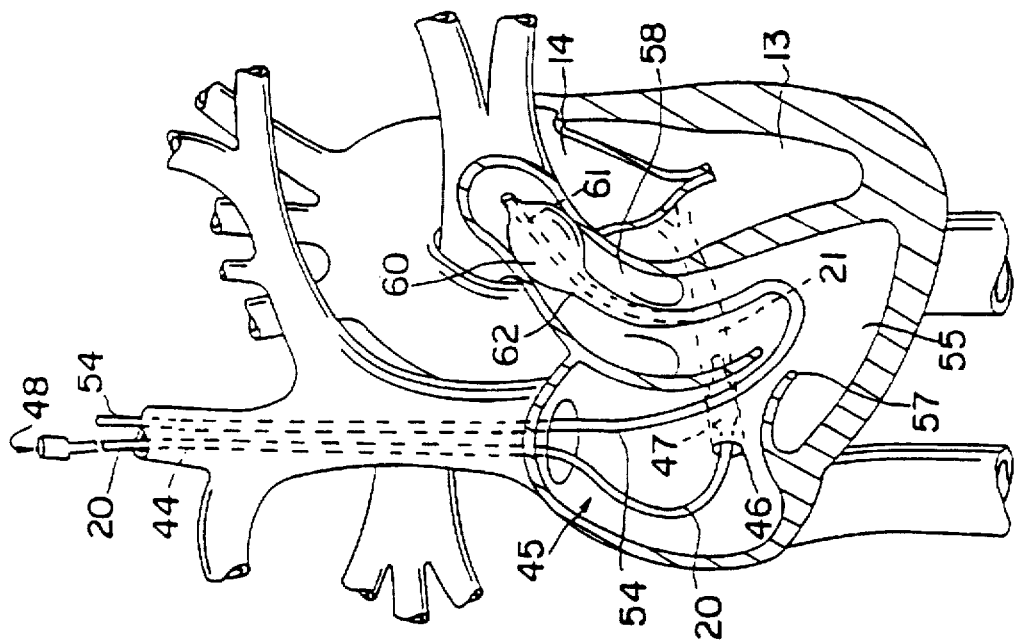
FIG. 4 is an enlarged view, partially in section, of the cardioplegia delivery catheter and the pulmonary venting catheter shown in FIG. 1.

A pulmonary venting catheter 54 is also shown in FIG. 4 disposed within the right internal jugular vein 44 and extending through the right atrium 45 and right ventricle 55 into the pulmonary trunk 56. The catheter 54 passes through tricuspid valve 57 and pulmonary valve 58. An inflatable occluding balloon 60 may be provided as shown on a distal portion of the pulmonary venting catheter 54 which is inflated to occlude the pulmonary trunk 56 as shown. The pulmonary venting catheter 54 has a first inner lumen 61 which extends from the distal end of the catheter to the proximal end of the catheter which vents fluid from the pulmonary trunk 56 to outside the patient's body either for discharge or for passage to the blood recovery unit and thereby decompresses the left atrium 14 through the pulmonary capillary beds (not shown). The catheter 54 has a second inner lumen 62 which is adapted to direct inflation fluid to the interior of the inflatable balloon 60.

To set up the cardiac access system, the patient is initially placed under light general anesthesia. The withdrawal catheter 17 and the return catheter 19 of the cardiopulmonary by-pass system 18 are percutaneously introduced into the right femoral vein 16 and the right femoral artery 15, respectively. An incision 24 is also made in the left groin to expose the left femoral artery 23 and the aortic occluding catheter 10 is inserted into the left femoral artery through an incision therein and advanced upstream until the balloon 11 on the distal end of the occluding catheter 10 is properly positioned in the ascending aorta 12. Note that by-pass could similarly be established in the left groin and the aortic occlusion catheter put into the right femoral artery. The retrograde perfusion catheter 20 is percutaneously inserted by a suitable means such as the Seldinger technique into the right interior jugular vein 44 and advanced into the right atrium 45 and guided through the discharge opening 46 into the coronary sinus.

The pulmonary venting catheter 54 is advanced through the right internal jugular vein 44, the right atrium 45, and right ventricle 55, and into the pulmonary trunk 56. The occluding balloon 60 may be inflated if necessary by inflation with fluid passing through the lumen 62 to block the pulmonary trunk 56 and vent blood therein through the lumen 61 where it is discharged through the proximal end of the catheter which extends outside of the patient. The venting of the pulmonary trunk 56 results in the decompressing of the left atrium 14. In the alternative, the venting catheter 54 may be provided with means on the exterior thereof, such as expanded coils as described in U.S. Pat. No. 4,889,137 (Kolobow), which hold open the tricuspid and pulmonary valves and perform the same function of decompressing the left atrium. See also the article written by F. Rossi et. al. in the Journal of Thoracic Cardiovascular Surgery, 1900;100:914–921, entitled "Long-Term Cardiopulmonary Bypass By Peripheral Cannulation In A Model Of Total Heart Failure", which is incorporated herein in its entirety by reference.

The operation of the cardiopulmonary by-pass unit 18 is initiated to withdraw blood from the femoral vein 16 through catheter 17, remove $CO_2$ from and add oxygen to the withdrawn blood and then pump the oxygenated blood through the return catheter 19 to the right femoral artery 15. The balloon 11 may then be inflated to occlude the ascending aorta 12, causing the blood pumped out of the left ventricle (until the heart stops beating due to the cardioplegic fluid as discussed hereinafter) to flow through the discharge port 41 into the first inner lumen 40 of the occluding catheter. The blood flows through the inner lumen 40 and out the third arm 32 of the adapter 26 into the by-pass line 33 and then into the blood filter and blood recovery unit 37 through the valve 34 and line 36. For blood and irrigation fluids containing debris and the like, the position of the valve 34 may be changed to direct the fluid through the discharge line 35.

The balloon 47 on the distal extremity of the retroperfusion catheter 20 is inflated to occlude the coronary sinus 21 to prevent fluid loss through the discharge opening 46 into the right atrium 45. A liquid containing a cardioplegic agent such as KCl is directed through the catheter 20 into the coronary sinus 21 and the pressure and volumetric flow rate of the cardioplegic fluid within the coronary sinus 21 are maintained sufficiently high (e.g. at least 100 ml/min at about 40 mm Hg) so that the cardioplegic fluid will pass through the coronary veins, crossing the capillary beds to the coronary arteries 50 and 51 and out the ostia 52 and 53.

Cardioplegic fluid is delivered through the delivery catheter at a flow rate sufficient to maintain cardioplegic arrest by periodic or continual infusions. However, cardioplegic solution pressure within the coronary sinus should be less than about 50 mm Hg to avoid tissue damage. The preferred cardioplegic fluid is a mixture of blood and a cardioplegic agent such as an aqueous potassium chloride (KCl) solution, preferably at a ratio or four parts blood to one part KCl solution (by volume). The aqueous KCl solution consists of crystalloid KCl mixed with saline to have a concentration in the range of 10–50 mEq K+/liter, and preferably 15–30 mEq K+/liter. This KCl solution may be mixed into oxygenated blood received from the cardiopulmonary bypass system, typically having a hematocrit of around 25%. The cardioplegic solution is usually cooled in an ice bath to a temperature of between 6° C. and 10° C., resulting in a fluid with a viscosity in excess of 3.0 centipoise, and usually in the range of 6 to 8 centipoise. This cardioplegic fluid is directed to port 132 on the proximal end of delivery catheter 20, and delivered to the coronary sinus at a preferred flow rate of at least about 100 ml/min. and preferably about 200 ml/min. in order to maintain cardioplegic arrest. However, the pressure required to pump the cardioplegic fluid through the lumen of the delivery catheter ("pump pressure") should not exceed 300 mmHg so as to avoid excessive hemolysis of the blood component. Cardioplegic fluid flow through delivery catheter 20 is maintained on a periodic basis, e.g., about every 15–30 minutes for 2–4 minutes, so long as the heart is to remain under cardioplegic arrest.

It will be understood to those of skill in the art that cardioplegic fluid may be delivered at lower flow rates for longer periods, or more frequently, to obtain the same desired total volume of delivered fluid. Delivery at lower flow rates might allow the use of a delivery catheter having a delivery lumen with a cross-sectional area less than the preferred minimum area of 4 $mm^2$. However, in most cases it is desirable to deliver cardioplegic fluid less often, and the time required to deliver the desired volume of cardioplegic fluid should be minimized. Therefore, a delivery lumen of maximum area (while keeping the overall profile of the catheter small enough to allow transluminal positioning from a peripheral vein) is usually preferred.

Antegrade cardioplegic fluid delivery through aortic occlusion catheter 10 may be used in conjunction with retrograde delivery through delivery catheter 20. In one embodiment, an initial bolus about 1000–1500 ml of cardioplegic fluid is delivered through inner lumen 40 of aortic occlusion catheter 10 which initiates cardioplegic arrest, after which cardioplegic arrest is maintained by retrograde delivery through delivery catheter 20 on a continual or periodic basis.

Once the cardioplegic fluid passes through the capillary beds in the myocardium, the heart very quickly stops beating. At that point the myocardium is paralyzed and has very little demand for oxygen and can be maintained in this state for long periods of time with minimal damage.

It should be noted that the retrograde cardioplegia delivery catheter of the invention could be utilized with a conventional aortic cross-clamp instead of the occluding catheter 10 in an open surgical procedure, which could eliminate the need for aortic cannulation or reduce the size of the aortic cannula used for antegrade delivery of cardioplegic fluid. Moreover, the retrograde delivery catheter could be used with a thoracoscopic aortic cross-clamp for aortic occlusion as described in copending application Ser. No. 08/173,899, filed Dec. 27, 1993, to supplement or replace antegrade delivery of cardioplegic fluid.

With the cardiopulmonary by-pass system in operation, the heart completely paralyzed and not pumping, the left atrium decompressed and the ascending aorta blocked by the inflated balloon 11 on the occluding catheter 10, the heart is appropriately prepared for a cardiac procedure. The procedures with which the system and method of the invention are useful include thoracoscopic coronary artery bypass grafting, thoracoscopic or endovascular repair or replacement of the mitral, aortic and other valves, thoracoscopic repair of atrial or ventricular septal defects and other congenital defects, transmyocardial laser revascularization, electrophysiological mapping and ablation, and various other procedures which require or would benefit from the inducement of cardioplegic arrest. The invention may also be advantageous to induce cardioplegic arrest in conventional open surgical procedures as a substitute for the conventional external aortic cross-clamp and conventional cardioplegia cannula introduced directly into the heart and/or aorta.

Inflation of the inflatable member 11 on the distal end of the delivery catheter 10 fixes the distal end of the occluding catheter 10 within the ascending aorta 12 and isolates the left ventricle 13 and the upstream portion of the ascending aorta from the rest of the arterial system downstream from the inflatable member. The passage of any debris or emboli, solid or gaseous, generated during a cardiovascular procedure to regions downstream from the site would be precluded by the inflated balloon 11. Fluid containing debris or emboli can be removed from the region between the aortic valve and the occluding balloon 11 through the inner lumen 40 of catheter 10. A clear, compatible fluid, e.g. an aqueous based fluid such as saline delivered through the inner lumen 40 or the cardioplegic fluid discharging from the coronary ostia 52 and 53, may be maintained in the region wherein the cardiovascular procedure is to be performed to facilitate use of an angioscope or other imaging means that allows for direct observation of the cardiac procedure. Preferably, the fluid pressure in the left ventricle 13 is maintained sufficiently higher than that in the left atrium to prevent blood from the left atrium from seeping into the left ventricle and interfering with the observation of the procedure. The inner lumen 40 is dimensioned to allow for the passage of instruments used during the cardiac procedure such as a tissue cutter, an angioscope, and tubes used for infusing irrigation fluid and for aspirating debris, thrombus and the like, and for the introduction of a prosthetic device, such as a heart valve.

Figure 5:
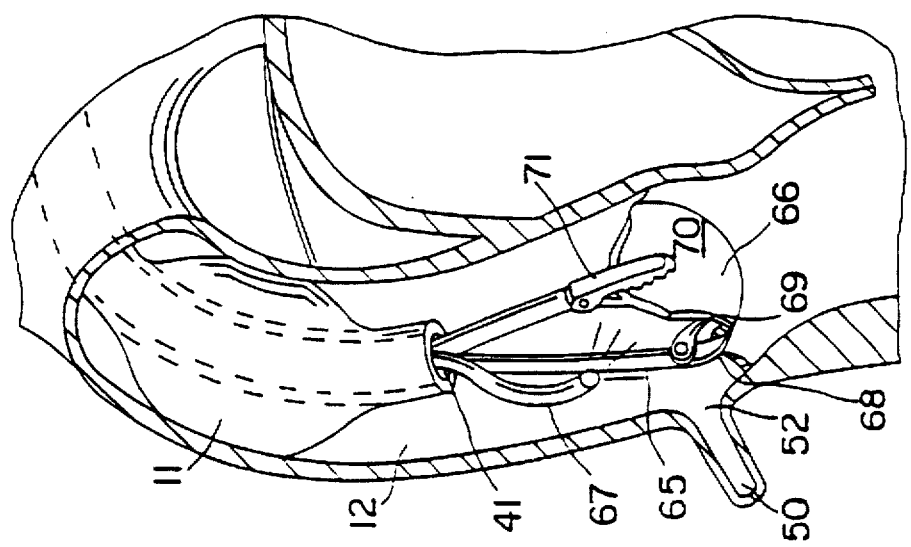
FIG. 5 is an elevational view, partially in section of the occluding catheter shown in FIG. 2 schematically illustrating the removal of an aortic heart valve.

The cardiac accessing system of the invention is particularly useful in the removal of the aortic heart valve and replacement thereof with a prosthetic heart valve which is illustrated in FIGS. 5 through 8. As shown in FIG. 5, a tissue cutter 65 is inserted into the patient through the inner lumen 40 of the occluding catheter 10 and advanced therein to the site of the aortic valve 66 which is to be removed. An angioscope 67 is likewise advanced through the inner lumen 40 until the distal end thereof extends out of the distal end of the occluding catheter 10. At least one of the cutting blades 68 and 69 on the tissue cutter 65 is actuated from the proximal end thereof which extends out of the second arm 30 of the adapter 26 on the proximal end of the catheter 10. The guidance and operation of the cutter 65 is controlled by the physician or other operator while observing the cutter through the angioscope 67. Due to its size and condition, the aortic valve 66 will usually have to be cut into smaller sections, such as section 70 as shown, so that it will fit within the inner lumen 40 of the occluding catheter 10 in order to remove the valve material from the patient. Preferably, forceps 71 or other suitable grasping means are employed to hold onto the aortic valve sections as they are severed by the cutting means 65 to ensure that the valve sections are accurately severed from the site with little or no damage to the underlying tissue of the ascending aorta and removed through the inner lumen 40. The cutting means 65 may have to be withdrawn from the occluding catheter 10 before large severed portions of the aortic valve 66 can be removed by forceps 71. During the procedure a continuous flow of clear liquid, such as the clear cardioplegic fluid exiting the ostia 52 and 53 and/or fluid being infused via the clamp 10 or an angioscope 67, is maintained to facilitate the observation of the region by the operator using the angioscope 67. After the valve 66 has been severed and removed from the region, the instruments used for this particular procedure are withdrawn from the patient through the inner lumen 40 of the occluding catheter 10. Instead of or in addition to mechanical cutting means, laser, electrosurgery, or other cutting methods may be employed in the valve removal procedure.

Direct observation of the placement of the cutting device 65 by suitable imaging means such as an angioscope 67 will ensure accurate positioning of the cutter blades 68 and 69 against the aortic valve to more effectively sever the valve 66 with little or no damage to the supporting aortic tissue. Aortic damage might interfere with the placement of a replacement valve 72 at the site. The precision of the valve removal and replacement is important to the success of endovascular valve replacement. There are several imaging techniques presently available, in addition to the angioscopic technique described, which provide complementary options to assure this precision, namely 1) transesophageal echocardiography; 2) intravascular ultrasound passed through the inner lumen of the delivery catheter 10; 3) intravascular ultrasound or angioscopy passed intravascularly via the venous system through the intra-atrial septum, across the mitral valve, and into the left ventricle; and 4) fluoroscopy. Note that an angioscope within the left ventricle would provide both the added benefit of allowing constant high definition imaging of the entire procedure and high-flow irrigation.

Figure 6:
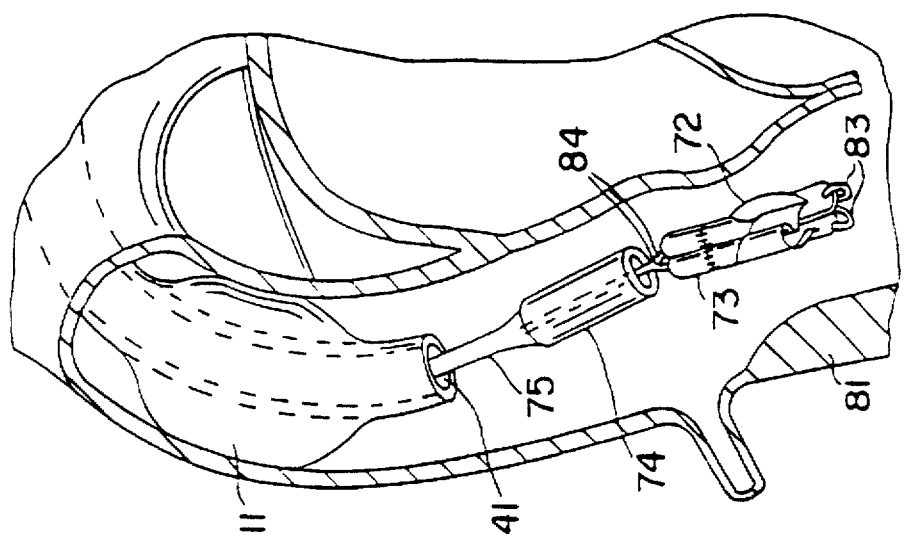
FIG. 6 schematically illustrates the introduction of a prosthetic valve into the region of the ascending aorta from which the original heart valve had been removed.

After the heart valve 66 is removed, a replacement valve 72 is then advanced through the inner lumen 40 of the occluding catheter 10 as shown in FIG. 6. The valve 72 is preferably a bioprosthetic valve such as xenograft valve. Porcine glutaraldehyde preserved valves are quite suitable because, as previously mentioned, they are readily accessible, they are storable, and they are available in a variety of sizes. The replacement valve 72, which is shown in FIG. 6 in an inverted and folded condition, has a Dacron skirt 73 secured to the lower rim of the natural porcine valve to facilitate securing the replacement valve to the wall of ascending aorta 12 at or near to the site from which the original aortic valve 66 was removed. The folded and inverted replacement valve 72 is disposed within the expanded end 74 of valve delivery catheter 75 so that the valve 72 can be advanced through the occluding catheter 10. The valve 72 is urged out of the expanded end 74 by the connector cables 84 which are connected to the upper extensions of the valve by releasable means 83. Once outside of the expanded end 74, the valve 72 expands due to the natural resiliency of the valve and the connector cables. The valve delivery catheter 75 is then removed by withdrawing it through the inner lumen 40 of the occluding catheter 10. Alternatively, the valve 72 may be provided with a temporary or permanent expandable support frame. The frame may contain stapling elements to secure the valve to the aortic wall.

Figure 7:
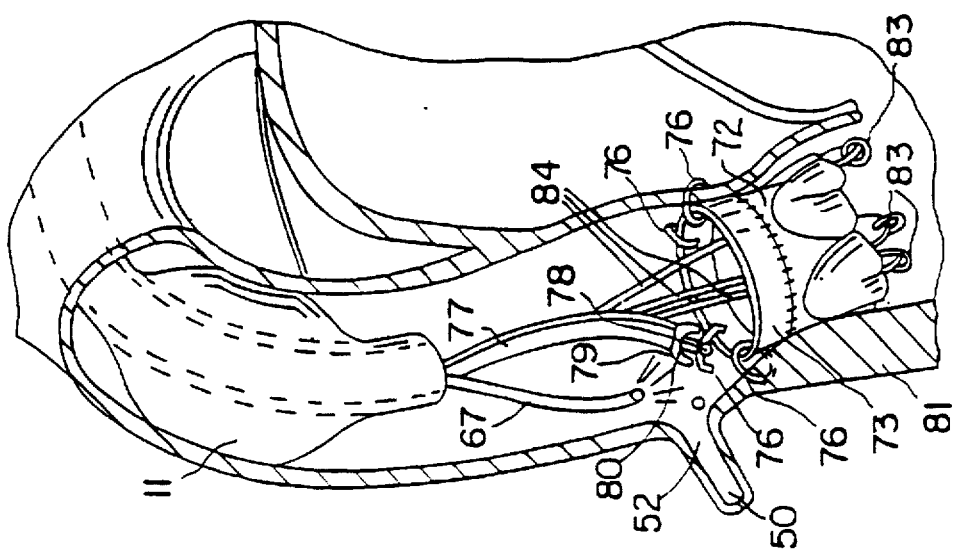
FIG. 7 schematically illustrates securing a mounting skirt on the prosthetic valve to the wall of the ascending aorta.

The Dacron skirt 73 is fixed to the aortic root 12 by means of a plurality of staples 76, as shown in FIG. 7, which are secured by the stapling mechanism 77 which is advanced through the inner lumen 40 and out of the distal port 41. The stapling mechanism 77 has an L-shaped holding arm 78 that holds the staple 76 and shaping member 79 having an arcuate shaping surface 80 which presses the staple 76 against holding arm 78 deforming the staple as it is pushed through the Dacron skirt 73 and into the aortic wall 81 as shown to force the pointed arms or tines thereof toward each other and fix the staple within the aortic wall. In the alternative the holding arm 78 may be moved toward the shaping member 79 or both may be advanced toward each other. The stapling mechanism 77 is preferably provided with a removable protective sheath (not shown) to facilitate the advancement of the mechanism through the inner lumen 40 without the pointed ends or tines of the staples 76 sticking into the inner wall of the occluding catheter 10 which defines the inner lumen 40. Usually about 10 to about 20 staples will be required to adequately secure the skirt 73 to the aortic wall 81. The angioscope 67 is provided to allow the physician to observe the procedure and guide the stapling mechanism 77 to the desired location and to secure the staple 76 and the skirt 73 at the desired location within the aortic root 12.

Figure 8:
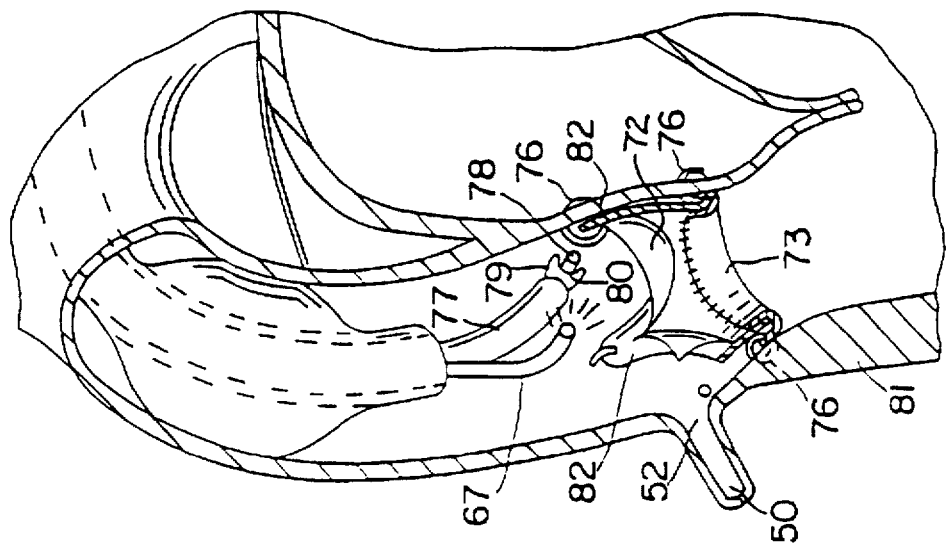
FIG. 8 schematically illustrates securing the upper extensions of the valve to the aortic wall.

Once the Dacron skirt 73 is properly secured, the inverted valve 72 is pulled through the fixed Dacron skirt 73, as shown in FIG. 8, and the upper extensions of the new valve 72 are stapled in essentially the same manner as the Dacron skirt 73. Care must be exercised when placing the Dacron skirt 73 prior to securing it to the aortic wall 81 so that when the inverted portion of the new valve 72 is pulled through the secured Dacron skirt 73, the ostia 52 and 53 of the coronary arteries 50 and 51 are not blocked by the upper extensions 82 of the valve 72. After the upper extensions 82 are secured to the aortic wall 81, the releasable means 83 at the end of the connector cables 84 are released and the cables are withdrawn through the inner lumen 40 of the occluding catheter 10.

Any tissue debris resulting from the aortic valve removal and new valve placement is trapped by the barrier formed by the inflated balloon 11 on the distal end of the occluding catheter 10. However, liquid in the aortic region containing such debris may be removed through an aspiration tube (not shown) disposed within the inner lumen 40 of the occluding catheter 10 or through inner lumen 40 by aspirating the fluid containing the debris. An irrigation catheter may be used to dislodge any debris caught between the inflated balloon 11 and the aortic wall where the two meet.

When the replacement valve 72 is secured in place, the fluid pumped through the retroperfusion catheter 20 is changed to a compatible fluid, e.g. saline or blood, containing no cardioplegic agents in order to flush out the cardioplegic materials from the myocardium through the ostia 52 and 53. The pulmonary venting catheter 54 may also be removed at the same time. Shortly thereafter the heart begins to beat on its own or it is externally defibrillated and the blood coming into the right heart is pumped through the pulmonary trunk to the lungs where it is oxygenated in the normal fashion. Oxygenated blood is returned from the lungs into the left atrium and is then pumped from the left ventricle through the new valve into the ascending aorta. Initially, the balloon 11 is maintained in the inflated condition, forcing the blood pumped out of the left ventricle to pass through the region of the ascending aorta 12 into inner lumen 40 of the occluding catheter 10 taking with it debris, emboli and the like. The blood passing through inner lumen 40 is directed through the third arm 32 of adapter 26, through the valve 34 and line 36 leading to blood filter and recovery unit 37 where the blood may be filtered and returned to the patient through the cardiopulmonary by-pass system 18. Alternatively, the position of the valve 34 may be changed by means of arm 85 to discharge blood or other fluid containing tissue, emboli, debris and the like through discharge line 35. After sufficient time has elapsed to ensure that debris and embolus free oxygenated blood is being pumped out of the left ventricle 13 the balloon 11 is deflated to allow natural blood flow through the aorta and the cardiopulmonary by-pass system 18 is shut down.

The occluding catheter shaft 39 may be formed of conventional materials such as polyethylene, polyvinyl chloride and the like. Balloon 11 may be formed of materials such as latex, silicone, C-Flex, or the like. Preferably, the balloon 11 is elastic, so as to expand to and circumferentially occlude the vessel into which it is positioned when fluid pressure is applied to the balloon. Alternatively, the balloon 11 may be formed of polymers such as polyethylene, polyethylene terephthalate, or a polyolefinic ionomer such as Surlyn®, which is available from E. I. DuPont, DeNemours & Co. Such a balloon would be relatively inelastic when inflated, so as to inflate to a predetermined size and maintain essentially that size even when additional fluid pressure is applied within the interior of the balloon. The balloon 11 will generally have an expanded diameter of about 20 to 40 mm to effectively occlude the patient's ascending aorta and an expanded length of about 2 to about 10 cm so as to be disposed between the coronary ostia and the brachiocephalic artery without blocking these arteries. The overall length of the occluding catheter should be at least 80 cm to facilitate passage through the femoral or brachiocephalic arteries to the ascending aorta.

The retroperfusion catheter 20 may be a commercially available retroperfusion catheter. There are suitable cardiopulmonary by-pass systems available commercially.

For a brief discussion of cardiopulmonary by-pass systems reference is made to Weber, John G., *Encyclopedia of Medical Devices and Instrumentation*, Vol. 3, pp. 1440–1457.

Figure 10:
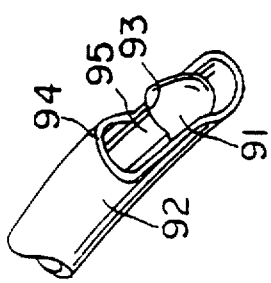
FIG. 10 is an enlarged perspective view of the cutting member of the catheter shown in FIG. 9.
Figure 9:
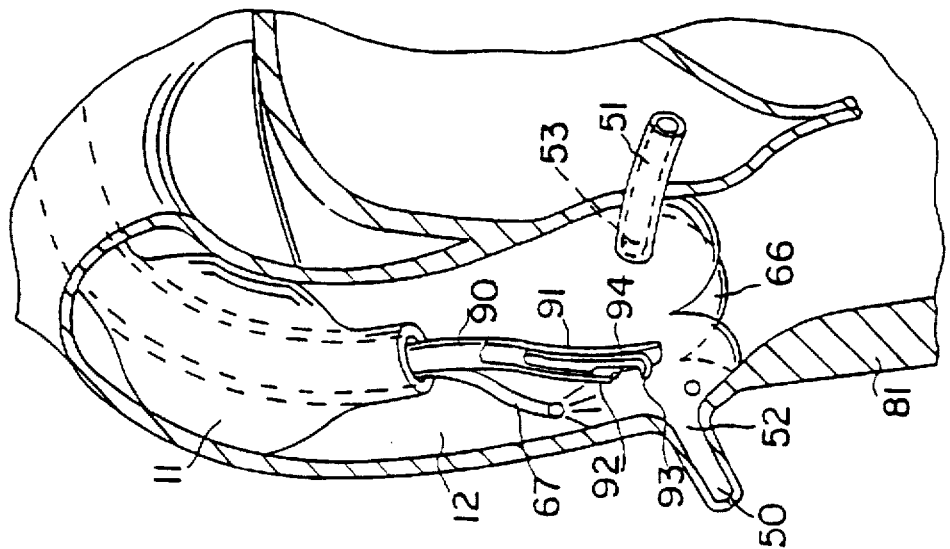
FIG. 9 schematically illustrates an alternate means for removing a heart valve.

An alternative tissue cutting system is depicted in FIGS. 9 and 10. In this embodiment catheter 90 is provided with a cutting head 91 which is slidably disposed within the cutter housing 92. The cutting head 91 is provided with a cutting edge 93 and cutter housing 92 is provided with cutting edge 94. The distal end of the catheter 90 is urged against tissue which is to be removed so that the tissue is pressed into the receiving chamber 95 within the cutting head 91. The cutting head 91 is slidably withdrawn from the cutter housing 92 so that the cutting edge 93 slides by the cutting edge 94 in a cutting relationship so as to sever the tissue within the receiving chamber 95. The severed tissue may be removed by aspiration or the cutting head 91 may be withdrawn from the patient and the severed tissue may be manually or otherwise removed. Preferably, the positioning of the distal end of catheter 90 and the urging of the cutting head against the tissue to be removed is observed by the physician or other operator through angioscope 67 or other suitable imaging system as previously described.

Figure 11:
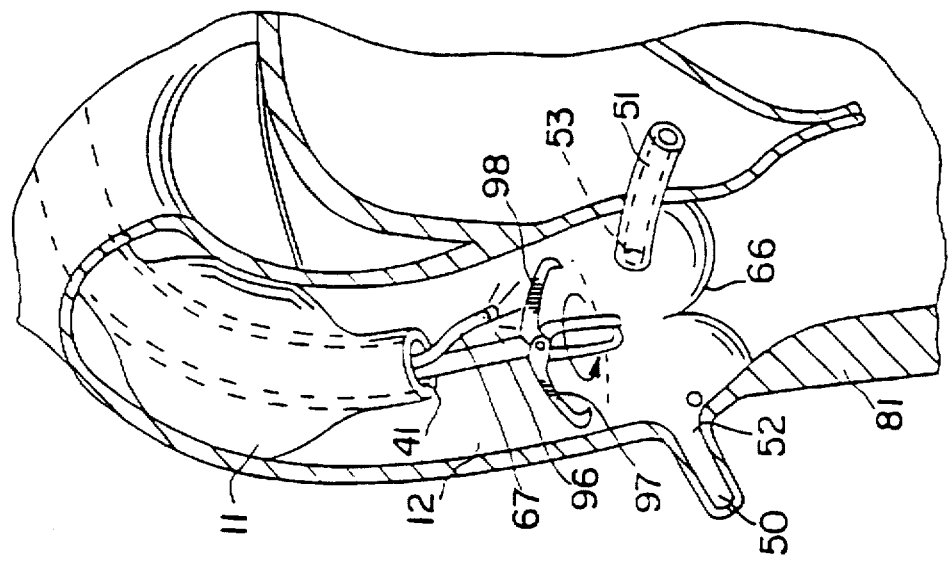
FIG. 11 schematically illustrates another alternate means for removing a heart valve.

Another cutting system 96, which is shown in FIG. 11, has expandable cutting blades 97 and 98 which are biased or otherwise adapted to expand to a cutting position as shown and rotated at high rotational speeds by a drive shaft and then pressed against the tissue to be severed. The blades 97 and 98 may be biased to expand outwardly by a spring (not shown) or the blades may be forced outwardly by the high speed rotation thereof. This cutting operation is likewise preferably observed by the physician or other operator to ensure proper cutting of the tissue to be removed.

Figure 12:
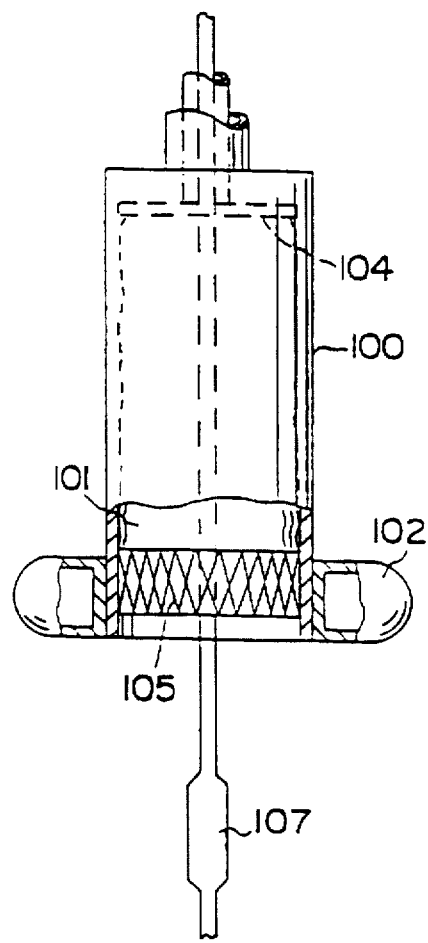
FIGS. 12 and 13 schematically illustrate an alternate embodiment of a valve introducing device and the method of discharging a prosthetic or replacement valve.
Figure 13:
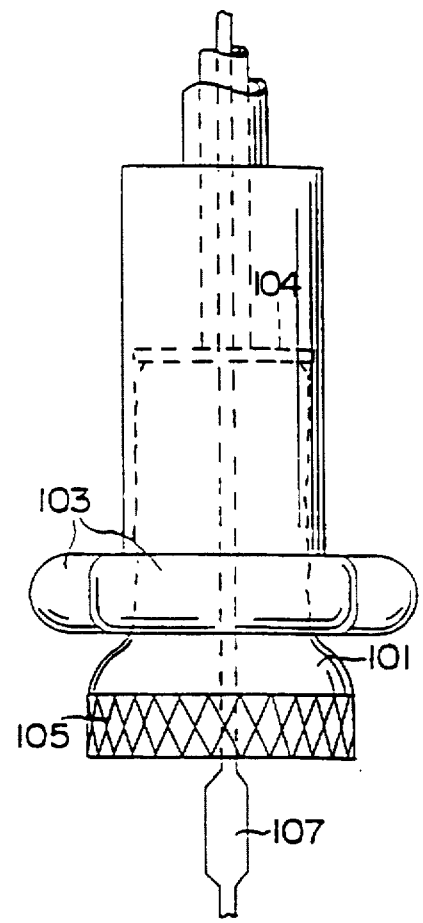

An alternative valve introducer device 100 is shown in FIGS. 12–13 which is adapted to contain a prosthetic or replacement valve 101 within expanded distal portion 102. The introducer device 100 may be introduced by itself or through the inner lumen of the occluding delivery catheter such as previously described until the enlarged distal portion 102 is located at or extends out of the distal end of the delivery catheter. The valve introducer device 100 may be provided with one or more positioning balloons 103 surrounding the expanded distal end 102 thereof which may be inflated in a differential manner, to assure accurate positioning of a prosthetic valve 101 when delivered out of the expanded distal end. A means, such as piston 104 is provided to push the replacement valve 101 out of the expanded distal end 102 when it is in the appropriate position within the patient's ascending aorta. Forceps or other holding means as previously described may be used to position the replacement valve 101 within the location from which the original valve has been removed.

Figure 14:
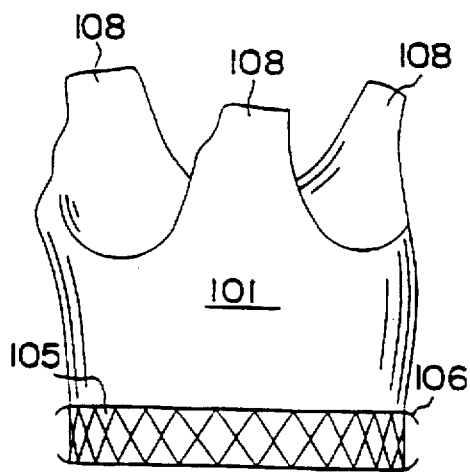
FIG. 14 schematically represents in an elevational view a prosthetic heart valve.
Figure 15:
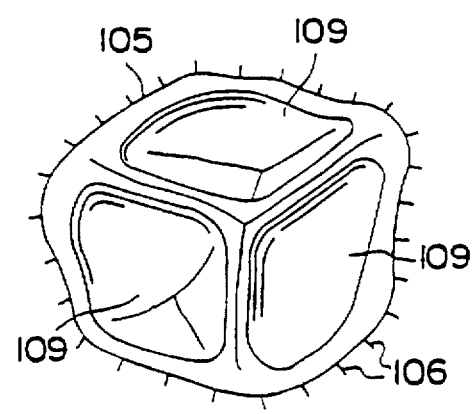
FIG. 15 is a top view of the prosthetic heart valve shown in FIG. 14.

An alternative replacement or prosthetic valve 101 is best shown in the expanded condition in FIGS. 14 and 15. As indicated, the valve 101 is provided with a cylindrical base 105 having mounting staples 106 which can be pressed into the wall portion of the ascending aorta at the desired situs by means of an expandable inelastic balloon 107 which is inflated within the valve 101. The upper extensions 108 of the replacement valve 101 from which the leaves or cusps 109 are supported are for the most part self supporting and may not require securing to the wall section of the ascending aorta. The valve introducer device 100 and the inflatable balloon 107 which when inflated presses the mounting staples 106 into the aortic wall may, when deflated, be withdrawn through the inner lumen of a delivery catheter. The aortic region between the site of the replacement valve and the delivery catheter may be well irrigated to remove debris, emboli and the like before regular blood flow through the region is resumed.

The invention provides several benefits, including the ability to endovascularly replace existing cardiac valves or perform other cardiac procedures while avoiding the riskier, more expensive and more traumatic open-heart surgical procedure.

The replacement prosthetic valve device is preferably a bioprosthetic device because these valves do not require the patient to undertake life-long anticoagulant therapy as do mechanical valves. Once inserted, the bioprosthetic valve is capable of operating autonomously. The useful life of a bioprosthetic valve placed via the endovascular procedure may extend to over twenty years, and since most of the valve procedures are performed on the elderly, the bioprosthetic valve will usually function well throughout the remaining life of the patient.

Once the endovascular implantation of the prosthetic valve device is completed in the patient, the function of the prosthetic valve device can be monitored by the same methods as used to monitor valve replacements done by open-heart surgery. Routine physical examination, angiography, or periodic echocardiography can be performed. In contrast to open-heart surgery, however, the patient will recover in a very short period when his or her aortic valve is endovascularly removed and replaced with a prosthetic valve. The replacement valve device can be used in any patient where bioprosthetic valves are indicated, and is particularly suitable for elderly patients and patients unable to tolerate open-heart procedures or life-long anticoagulation.

Unless described otherwise, the various components of the system of the present invention can be formed of conventional materials using conventional manufacturing techniques. The dimensions of the various components are selected so that they perform their intended functions in their intended environment.

While the present invention has been described herein in terms of certain preferred embodiments, it will be apparent to one of ordinary skill in the art that many modifications and improvements can be made to the invention without departing from the scope thereof.

What is claimed is:

1. A method of inducing cardioplegic arrest of a patient's heart, the heart having an aorta leading away therefrom to a peripheral artery, coronary arteries in communication with the aorta, and a brachiocephalic artery in communication with the aorta downstream from the coronary arteries, the method comprising:
   providing a retrograde delivery catheter having an occluding member, the occluding member having a collapsed shape and an expanded shape, the retrograde delivery catheter also having a lumen and an outlet positioned distal to the occluding member for delivering a fluid to a patient's coronary sinus;
   inserting the retrograde delivery catheter through a peripheral vein in the patient;
   advancing the retrograde delivery catheter transluminally through the vein and into the patient's coronary sinus;
   expanding the occluding member to thereby occlude the patient's coronary sinus; and
   delivering a cardioplegic fluid comprising blood and a cardioplegic agent through the retrograde delivery catheter to the coronary sinus at a flow rate of at least 200 ml/min. and at a pump pressure of less than 300 mm Hg.

2. The method of claim 1 wherein the cardioplegic fluid has a viscosity of at least about 3.0 centipoise.

3. The method of claim 1 wherein the cardioplegic fluid comprises a mixture of blood and a cardioplegic agent in a ratio of at least about two parts blood to one part cardioplegic agent by volume.

4. The method of claim 3 wherein the cardioplegic agent comprises an aqueous KCl solution.

5. The method of claim 1 wherein the cardioplegic fluid is cooled to a temperature of 3° C.–10° C. before delivery to the coronary sinus.

6. The method of claim 1 wherein the advancing step is carried out with the retrograde delivery catheter being introduced over a guidewire slidably positioned in a lumen in the retrograde delivery catheter.

7. The method of claim 1 wherein the retrograde delivery catheter has at least two bends in a distal portion thereof, the method further comprising straightening the at least two bends during the advancing step.

8. The method of claim 1 wherein the advancing step comprises using fluoroscopy to observe the position of the retrograde delivery catheter in the heart.

9. The method of claim 8 wherein the advancing step further comprises injecting a radiopaque contrast fluid through the retrograde delivery catheter to determine the position thereof using fluoroscopy.

10. The method of claim 1 further comprising the steps of:
    withdrawing blood from a peripheral vein;
    oxygenating the withdrawn blood from the peripheral vein;
    returning the oxygenated blood to a peripheral artery; and
    isolating the coronary arteries from the oxygenated blood returned to the peripheral artery;
    wherein the isolating step includes the steps of positioning an endoaortic catheter in a peripheral artery, advancing the endoaortic catheter into the aorta, and expanding an expanding member on the distal end of the endoaortic catheter to occlude an aortic lumen between the coronary arteries and the brachiocephalic artery.

11. The method of claim 10 wherein the step of venting comprises withdrawing fluid from the aortic lumen upstream of the expandable member through a lumen in the endoaortic catheter.

12. The method of claim 10 further comprising the step of venting the heart of fluid, wherein the venting step includes withdrawing fluid from a pulmonary artery through a venting catheter positioned in a peripheral vein and extending transluminally through the heart into the pulmonary artery.

13. A method of delivering a fluid to a coronary sinus of a patient's heart, the method comprising:

positioning a retrograde delivery catheter in a peripheral vein and advancing the retrograde delivery catheter transluminally into the coronary sinus; and delivering the fluid to the coronary sinus through a lumen in the retrograde delivery catheter, the lumen having a cross-sectional area of no less than 4 mm$^2$ at any location along the retrograde delivery catheter.

14. The method of claim 13 wherein the fluid has a viscosity of at least 3.0 centipoise.

15. The method of claim 14 wherein the fluid is delivered at a flow rate of at least 200 ml/min, at a pump pressure of less than 300 mmHg.

16. The method of claim 13 wherein the fluid comprises a cardioplegic fluid, the method further comprising supporting the patient on cardiopulmonary bypass during the step of delivering.

17. The method of claim 13 wherein the step of positioning comprises using fluoroscopy to observe the position of the retrograde delivery catheter in the heart.

18. The method of claim 17 wherein the positioning step further comprises injecting a radiopaque contrast fluid through the retrograde delivery catheter to determine the position thereof using fluoroscopy.

19. A method of inducing cardioplegic arrest of a patient's heart, the heart having an aorta leading away therefrom to a peripheral artery, coronary arteries in communication with the aorta, and a brachiocephalic artery in communication with the aorta downstream from the coronary arteries, the method comprising:

providing a retrograde delivery catheter having an occluding member, the occluding member having a collapsed shape and an expanded shape, the retrograde delivery catheter having a lumen and an outlet positioned distal to the occluding member for delivering a fluid to the patient's coronary sinus;

inserting the retrograde delivery catheter through a vein in the patient;

advancing the retrograde delivery catheter transluminally through the vein and into the patient's coronary sinus;

expanding the occluding member to occlude the patient's coronary sinus; and delivering a cardioplegic fluid comprising blood and a cardioplegic agent through the lumen of the retrograde delivery catheter to the coronary sinus.

20. The method of claim 19, wherein:

the inserting step is carried out with the retrograde delivery catheter including a distal portion having an outer diameter of less than about 4.6 mm, the distal portion having a length of at least 50 cm proximal to the distal end.

21. The method of claim 19, wherein:

the delivering step is carried out with the lumen being configured to deliver a fluid having a viscosity of at least about 3.0 centipoise at a flow rate of at least 200 ml/min, and at a pump pressure of less than 300 mm.

22. The method of claim 19, wherein:

the inserting step is carried out with the retrograde delivery catheter including a shaft having at least a first bend near the distal end of the shaft to facilitate positioning the distal end in the coronary sinus, the first bend being in a range of about 20° to 70° from a longitudinal axis of a proximal portion of the retrograde delivery catheter proximal to the first bend.

23. The method of claim 19, wherein:

the inserting step is carried out with the retrograde delivery catheter having a flexible, elongated shaft, the shaft having a first bend near the distal end of the shaft to facilitate positioning the distal end in the coronary sinus, the first bend being between 20 mm and 40 mm from the distal end.

24. The method of claim 19, wherein:

the inserting step is carried out with the retrograde delivery catheter including a shaft having a first bend near the distal end of the shaft to facilitate positioning the distal end in the coronary sinus, the first bend being between 20 mm and 40 mm from the distal end, the shaft also having a second bend distal to the first bend.

25. The method of claim 19, wherein:

the inserting step is carried out with the retrograde delivery catheter having configured to deliver a fluid having a viscosity of at least about 3.0 centipoise at a flow rate of at least 200 ml/min, and at a pump pressure of less than 300 mm, an inflation lumen extending through the shaft, the expandable member including an inflatable balloon having an interior in communication with the inflation lumen, the balloon being configured to be inflatable to a size larger than the coronary sinus, the retrograde delivery catheter further including pressure limiting means to maintain inflation pressure of the balloon below a predetermined value selected to avoid injury to coronary sinus tissue.

26. A method of inducing cardioplegic arrest of a patient's heart, the heart having an aorta leading away therefrom to a peripheral artery, coronary arteries in communication with the aorta, and a brachiocephalic artery in communication with the aorta downstream from the coronary arteries, the method comprising:

providing a retrograde delivery catheter having an occluding member, the occluding member having a collapsed shape and an expanded shape, the retrograde delivery catheter also having a lumen and an outlet positioned distal to the occluding member for delivering a fluid to a patient's coronary sinus;

inserting the retrograde delivery catheter through a peripheral vein in the patient;

advancing the retrograde delivery catheter transluminally through the vein and into the patient's coronary sinus;

expanding the occluding member to thereby occlude the patient's coronary sinus;

delivering a cardioplegic fluid comprising blood and a cardioplegic agent through the retrograde delivery catheter to the coronary sinus;

positioning an aortic occlusion device in the patient's ascending aorta, the aortic occlusion device having an occluding member;

expanding an expanding member on the distal end of the endoaortic catheter to occlude an aortic lumen between the coronary arteries and the brachiocephalic artery; and delivering the cardioplegic fluid to the patient's ascending aorta through a lumen in the aortic occlusion device.

27. The method of claim 26 wherein the positioning step is carried out by passing the aortic occlusion device through a peripheral artery of the patient.

28. The method of claim 26 further comprising the step of venting the heart of fluid, wherein the venting step includes withdrawing fluid from a pulmonary artery through a venting catheter positioned in a peripheral vein and extending transluminally through the heart into the pulmonary artery.

* * * * *